(12) United States Patent
Thadani et al.

(10) Patent No.: US 8,143,451 B2
(45) Date of Patent: Mar. 27, 2012

(54) METHODS OF PREPARING TERTIARY CARBINAMINE COMPOUNDS

(75) Inventors: Avinash N. Thadani, Windsor (CA); Bhartesh Dhudshia, Windsor (CA)

(73) Assignee: Kanata Chemical Technologies Inc., Toronto, Ontario (CA)

( * ) Notice: Subject to any disclaimer, the term of this patent is extended or adjusted under 35 U.S.C. 154(b) by 787 days.

(21) Appl. No.: 11/867,222

(22) Filed: Oct. 4, 2007

(65) Prior Publication Data

US 2008/0139847 A1    Jun. 12, 2008

Related U.S. Application Data

(60) Provisional application No. 60/828,288, filed on Oct. 5, 2006.

(51) Int. Cl.
*C07C 211/00*    (2006.01)

(52) U.S. Cl. ......... 564/308; 564/336; 564/384; 564/471
(58) Field of Classification Search .................. None
See application file for complete search history.

(56) References Cited

OTHER PUBLICATIONS

Dhudshia et al, Chemical Communications, 2005, (44), 5551-5553.*
Kobayashi et al., *Chem. Commun.*, (2005), p. 104.
Sugiura et al., *J. Am. Chem. Soc.*, (2004), vol. 126, p. 7182.

* cited by examiner

*Primary Examiner* — Sudhakar Katakam
(74) *Attorney, Agent, or Firm* — Bereskin & Parr LLP/S.E.N.C.R.L., s.r.l.; Michael Fenwick

(57) ABSTRACT

The present invention relates to a method for the preparation of tertiary carbinamine compounds from diastereoselective allylation and crotylation of N-unsubstituted imines derived from ketones.

22 Claims, No Drawings

METHODS OF PREPARING TERTIARY CARBINAMINE COMPOUNDS

The present application claims the benefit of priority under 35 U.S.C. §119(e) from U.S. provisional patent application No. 60/828,288, filed Oct. 5, 2006.

FIELD OF THE INVENTION

The present invention relates to a method for the preparation of tertiary carbinamine compounds, particularly the preparation of tertiary carbinamine compounds, from diastereoselective allylation and crotylation of N-unsubstituted imines derived from ketones.

BACKGROUND OF THE INVENTION

Research into the addition of allyl organometallics to carbonyl compounds and their derivatives continues to proceed unabated—a consequence of the fact that the resulting homoallylic products have proven to be valuable synthons [S. E. Denmark and N. G. Almstead, Modern Carbonyl Chemistry, ed. J. Otera, Wiley-VCH, Weinheim, 2000, ch. 10; Y. Yamamoto and N. Asao, Chem. Rev., 1993, 93, 2207; and W. R. Roush, Comprehensive Organic Synthesis, ed. B. M. Trost, I. Fleming and C. H. Heathcock, Pergamon, Oxford, 2nd edn., 1991, vol. 2, pp 1-53]. The majority of the research, however, has focused on the addition of these organometallics to aldehydes. For example, the reaction of

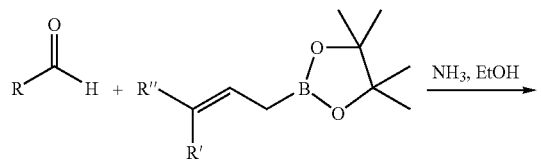

has previously been described by Kobayashi et al. [M. Sugiura, K. Hirano and S. Kobayashi, *J. Am. Chem. Soc.*, 2004, 126, 7182; S. Kobayashi, K. Hirano, M. Sugiura, *Chem. Commun.*, 2005, 104].

Although to a lesser extent, there have been some recent examples of allylation of ketones [L. F. Tietze, K. Schiemann, C. Wegner and C. Wulff, Chem. Eur. J., 1998, 4, 1862; S. Casolari, D. D'Addario and E. Tagliavini, Org. Lett., 1999, 1, 1061; R. Hamasaki, Y. Chounan, H. Horino and Y. Yamamoto, Tetrahedron Lett., 2000, 41, 9883; R. M. Kamble and V. K. Singh, Tetrahedron Lett., 2001, 42, 7525; J. G. Kim, K. M. Waltz, I. F. Garcia, D. Kwiatkowski and P. J. Walsh, J. Am. Chem. Soc., 2004, 126, 12580; T. R. Wu, L. Shen and J. M. Chong, Org. Lett., 2004, 6, 2701; and Y.-C. Teo, J.-D. Goh and T.-P. Loh, Org. Lett., 2005, 7, 2743]. Until recently, the expansion of the substrate scope to include imines and their derivatives had received limited attention. Some recent examples of the addition of allylorganometallics to aldimine derivatives can be found in the following references [C. Bellucci, P. G. Cozzi and A. Umani-Ronchi, Tetrahedron Lett., 1995, 36, 7289; H. Nakamura, K. Nakamura and Y. Yamamoto, J. Am. Chem. Soc., 1998, 120, 4242; F. Fang, M. Johannsen, S. Yao, N. Gathergood, R. G. Hazell and K. A. Jørgensen, J. Org. Chem., 1999, 64, 4844; T. Gastner, H. Ishitani, R. Akiyama and S. Kobayashi, Angew. Chem., Int. Ed., 2001, 40, 1896; H. C. Aspinall, J. S. Bissett, N. Greeves and D. Levin, Tetrahedron Lett., 2002, 43, 323; M. Sugiura, F. Robvieux and S. Kobayashi, Synlett, 2003, 1749; R. A. Fernandes and Y. Yamamoto, J. Org. Chem., 2004, 69, 735; S.-W. Li and R. A. Batey, Chem. Commun., 2004, 1382; I. Shibata, K. Nose, K. Sakamoto, M. Yasuda and A. Baba, J. Org. Chem., 2004, 69, 2185; and C. Ogawa, M. Sugiura and S. Kobayashi, Angew Chem., Int. Ed., 2004, 43, 6491]. As for the addition of allylorganometallics to ketimine derivatives, some recent examples have also been reported [C. Ogawa, M. Sugiura and S. Kobayashi, J. Org. Chem., 2002, 67, 5359; S. Yamasaki, K. Fujii, R. Wada, M. Kanai and M. Shibasaki, J. Am. Chem. Soc., 2002, 124, 6536; R. Berger, K. Duff and J. L. Leighton, J. Am. Chem. Soc., 2004, 126, 5686; H. Ding and G. K. Friestad, Synthesis, 2004, 2216].

However, there is yet no known synthetic methodology for the preparation of tertiary carbinamine compounds through diastereoselective allylation and crotylation of N-unsubstituted ketimines. New methodologies to solve the difficulties associated with making these valuable tertiary carbinamine compounds will no doubt have a tremendous impact in organic synthesis and in the chemical industry. New methodologies may also provide a new class of tertiary carbinamine compounds that cannot be obtained using conventional protocols. For example, the recent report of aminoallylation of aldehydes by Kobayshi and coworkers has already had a tremendous impact in organic synthesis [M. Sugiura, K. Hirano and S. Kobayashi, *J. Am. Chem. Soc.*, 2004, 126, 7182; S. Kobayashi, K. Hirano, M. Sugiura, *Chem. Commun.*, 2005, 104].

SUMMARY OF THE INVENTION

A new method for the preparation of tertiary carbinamine compounds from the diastereoselective allylation and crotylation of in situ generated N-unsubstituted ketimines has been developed. The method has been shown to provide the homoallylic amines in good to excellent yields through simple acid-base extraction. Also, the crotylation of N-unsubstituted ketimines has been shown to be highly diastereoselective.

Accordingly, the present invention relates to a method of preparing an amine of the formula Ia and/or Ib comprising reacting a compound of formula II with a compound of formula III:

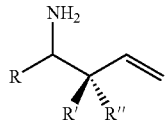

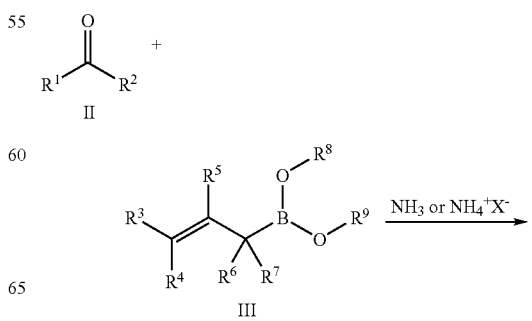

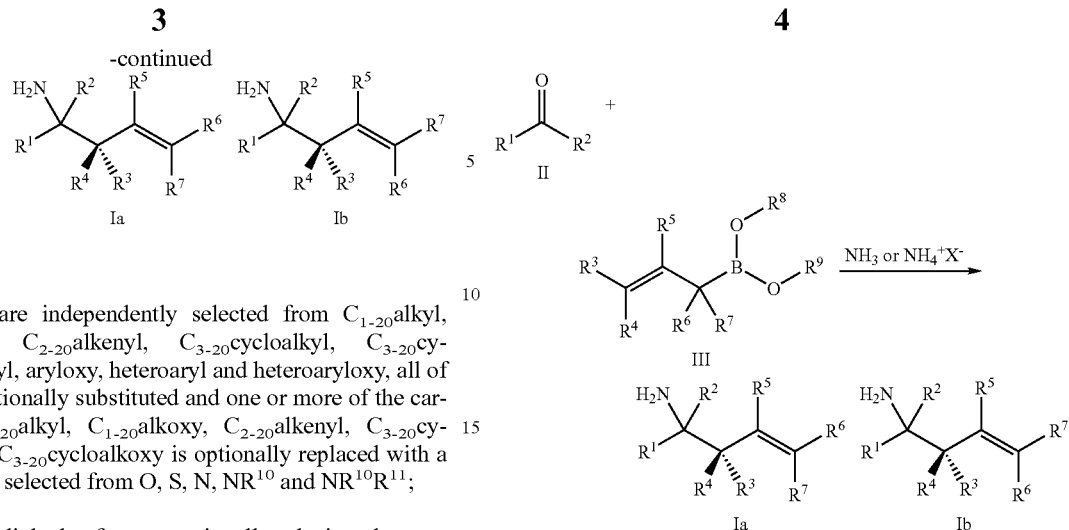

wherein
$R^1$ and $R^2$ are independently selected from $C_{1-20}$alkyl, $C_{1-20}$alkoxy, $C_{2-20}$alkenyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{3-20}$cycloalkyl and $C_{3-20}$cycloalkoxy is optionally replaced with a heteromoiety selected from O, S, N, $NR^{10}$ and $NR^{10}R^{11}$;
or
$R^1$ and $R^2$ are linked to form an optionally substituted monocyclic or polycyclic ring system having 4 to 20 atoms including the carbonyl to which $R^1$ and $R^2$ are bonded, and one or more of the carbons of the ring system is optionally replaced with a heteromoiety selected from O, S, N, $NR^{10}$ and $NR^{10}R^{11}$;
$R^3$ to $R^7$ are independently selected from H, $C_{1-20}$alkyl, $C_{1-20}$alkoxy, $C_{2-20}$alkenyl, $C_{3-20}$cycloalkyl, $C_{3-20}$cycloalkoxy, aryl, aryloxy, heteroaryl and heteroaryloxy, the latter 9 groups being optionally substituted and one or more of the carbons in $C_{1-20}$alkyl, $C_{1-20}$alkoxy, $C_{2-20}$alkenyl, $C_{3-20}$cycloalkyl and $C_{3-20}$cycloalkoxy, is optionally replaced with a heteromoiety selected from O, S, N, $NR^{10}$ and $NR^{10}R^{11}$;
$R^8$ and $R^9$ are independently selected from H, $C_{1-20}$alkyl, $C_{3-20}$cycloalkyl, aryl and heteroaryl, the latter 4 groups being optionally substituted;
or
$R^8$ and $R^9$ are linked to form an optionally substituted monocyclic or polycyclic ring system having 4 to 20 atoms, including the B and O atoms to which $R^8$ and $R^9$ are bonded;
$R^{10}$ and $R^{11}$ are independently selected from H, $C_{1-20}$alkyl, $C_{3-20}$cycloalkyl, aryl and heteroaryl, the latter 4 groups being optionally substituted,
in the presence of ammonia $NH_3$ or an ammonia equivalent of the formula $NH_4^+X^-$, wherein X is an anionic ligand.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

It has been demonstrated for the first time that tertiary carbinamine compounds can be efficiently and effectively generated through diastereoselective allylation and crotylation of N-unsubstituted imines that are derived from a diverse range of ketones. The method has been shown to be a simple three-component reaction of a ketone, excess ammonia or ammonia salt and an allylorganometallic reagent.

Accordingly, the present invention relates to a method of preparing an amine of the formula Ia and/or Ib comprising reacting a compound of formula II with a compound of formula III:

wherein
$R^1$ and $R^2$ are independently selected from $C_{1-20}$alkyl, $C_{1-20}$alkoxy, $C_{2-20}$alkenyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{3-20}$cycloalkyl and $C_{3-20}$cycloalkoxy, is optionally replaced with a heteromoiety selected from O, S, N, $NR^{10}$ and $NR^{10}R^{11}$;
or
$R^1$ and $R^2$ are linked to form an optionally substituted monocyclic or polycyclic ring system having 4 to 20 atoms including the carbonyl to which $R^1$ and $R^2$ are bonded, and one or more of the carbons of the ring system is optionally replaced with a heteromoiety selected from O, S, N, $NR^{10}$ and $NR^{10}R^{11}$;
$R^3$ to $R^7$ are independently selected from H, $C_{1-20}$alkyl, $C_{1-20}$alkoxy, $C_{2-20}$alkenyl, $C_{3-20}$cycloalkyl, $C_{3-20}$cycloalkoxy, aryl, aryloxy, heteroaryl and heteroaryloxy, the latter 9 groups being optionally substituted and one or more of the carbons in $C_{1-20}$alkyl, $C_{1-20}$alkoxy, $C_{2-20}$alkenyl, $C_{3-20}$cycloalkyl and $C_{3-20}$cycloalkoxy is optionally replaced with a heteromoiety selected from O, S, N, $NR^{10}$ and $NR^{10}R^{11}$;
$R^8$ and $R^9$ are independently selected from H, $C_{1-20}$alkyl, $C_{3-20}$cycloalkyl, aryl and heteroaryl, the latter 4 groups being optionally substituted;
or
$R^8$ and $R^9$ are linked to form an optionally substituted monocyclic or polycyclic ring system having 4 to 20 atoms, including the B and O atoms to which $R^8$ and $R^9$ are bonded;
$R^{10}$ and $R^{11}$ are independently selected from H, $C_{1-20}$alkyl, $C_{3-20}$cycloalkyl, aryl and heteroaryl, the latter 4 groups being optionally substituted,
in the presence of ammonia $NH_3$ or an ammonia equivalent of the formula $NH_4^+X^-$, wherein X is an anionic ligand.

The term "$C_{1-n}$alkyl" as used herein means straight and/or branched chain alkyl groups containing from one to n carbon atoms and includes, depending on the identity of n, methyl, ethyl, propyl, isopropyl, t-butyl, pentyl, hexyl, heptyl, octyl, nonyl, decyl, undecyl, dodecyl, hexadecyl, octadecyl, icosyl and the like and wherein n is an integer representing the maximum number of carbon atoms in the group.

The term "$C_{3-n}$cycloalkyl" as used herein means saturated cyclic or polycyclic alkyl groups containing from three to n carbon atoms and includes, depending on the identity of n, cyclopropyl, cyclobutyl, cyclopentyl, cyclohexyl, cycloheptyl, cyclooctyl, cyclononyl, cyclodecyl, cycloundecyl, cyclododecyl, cyclohexadecyl, cyclooctadecyl, cycloicosyl, adamantyl and the like, and wherein n is an integer representing the maximum number of carbon atoms in the group.

The term "$C_{1-n}$alkoxy" as used herein means straight and/or branched chain alkoxy groups containing from one to n carbon atoms and includes, depending on the identity of n, methoxy, ethoxy, propyoxy, isopropyloxy, t-butoxy, pentoxy, hexoxy, heptoxy, octoxy, nonoxy, decoxy, undecoxy, dodecoxy, hexadecoxy, octadecoxy, icosoxy and the like, and wherein n is an integer representing the maximum number of carbon atoms in the group.

The term "$C_{3-n}$cycloalkoxy" as used herein means saturated cyclic or polycyclic alkyoxy groups containing from three to n carbon atoms and includes, depending on the identity of n, cyclopropoxy, cyclobutoxy, cyclopentoxy, cyclohexoxy, cycloheptoxy, cyclooctoxy, cyclononoxy, cyclodecoxy, cycloundecoxy, cyclododecoxy, cyclohexadecoxy, cyclooctadecoxy, cycloicosoxy and the like, and wherein n is an integer representing the maximum number of carbon atoms in the group.

The term "$C_{2-n}$alkenyl" as used herein means straight and/or branched chain alkenyl groups containing from two to n carbon atoms and one to six double bonds and includes, depending on the identity of n, vinyl, allyl, 1-butenyl, 2-hexenyl and the like, and wherein n is an integer representing the maximum number of carbon atoms in the group.

The term "aryl" as used herein means a monocyclic or polycyclic carbocyclic ring system containing one or two aromatic rings and from 6 to 14 carbon atoms and includes phenyl, naphthyl, anthraceneyl, 1,2-dihydronaphthyl, 1,2,3,4-tetrahydronaphthyl, fluorenyl, indanyl, indenyl and the like.

The term "heteroaryl" as used herein means mono- or polycyclic heteroaromatic radicals containing from 5 to 14 atoms, of which 1 to 4 atoms are a heteroatom selected from nitrogen, oxygen and sulfur and includes furanyl, thienyl, pyrrolo, pyridyl, indolo, benzofuranyl and the like.

The term "halo" as used herein means halogen and includes chloro, fluoro, bromo and iodo.

The term "one or more" as used herein means that from one to the maximum allowable substitutions are allowed.

The present invention includes combinations of groups and substituents that are permitted and would provide a stable chemical entity according to standard chemical knowledge as would be known to those skilled in the art.

The term "polycyclic" or "ring system" as used herein means a cyclic group containing more than one ring in its structure, and includes bicyclic, tricyclic, bridged and spiro ring systems and the like.

It is an embodiment of the invention that the compounds of formulae Ia, Ib and II include those in which $R^1$ and $R^2$ are independently selected from $C_{1-10}$alkyl, $C_{2-10}$alkenyl, aryl and heteroaryl, all of which are optionally substituted. In a further embodiment of the invention, $R^1$ and $R^2$ in the compounds of the formulae Ia, Ib and II are independently selected from methyl, ethyl, propyl, butyl, pentyl, ethene, styrene, phenyl, benzyl, thiophene and indole, all of which are optionally substituted.

It is another embodiment of the invention that the compounds of formulae Ia, Ib and II include those in which $R^1$ and $R^2$ are linked to form an optionally substituted monocyclic or polycyclic ring system having 6 to 16 carbon atoms including the carbonyl to which $R^1$ and $R^2$ are bonded. In a further embodiment of the invention, one or more of the carbons of this ring system is optionally replaced with a heteromoiety selected from O, S, N, $NR^{10}$ and $NR^{10}R^{11}$, in which $R^{10}$ and $R^{11}$ are independently selected from H, $C_{1-6}$alkyl and aryl. In a still further embodiment of the invention, $R^1$ and $R^2$ in the compounds of the formulae Ia, Ib and II are linked to form a ring system selected from cyclohexane, bicyclo[2.2.1]heptane, bicyclo[3.1.1]hept-2-ene and fluorene, all of which are optionally substituted, and/or one or more of the carbons of cyclohexane, bicyclo[2.2.1]heptane, bicyclo[3.1.1]hept-2-ene or fluorene is optionally replaced with a heteromoiety selected from O, S, N and $NR^{10}$; in which $R^{10}$ is H or benzyl.

In an embodiment of the invention, the optional substituents on $R^1$ and $R^2$ in the compounds of the formulae Ia, Ib and II are independently selected from OH, halo, CN, $NO_2$, phenyl, benzyl, $OC_{1-6}$alkoxy, $C_{1-6}$alkyl, $C_{1-6}$alkenyl, $C_{1-6}$alkenyloxy, $NH_2$, $NH(C_{1-6}alkyl)$, $N(C_{1-6}alkyl)(C_{1-6}alkyl)$, $C(O)C_{1-6}$alkyl, $C(O)OC_{1-6}$alkyl, $SO_2C_{1-6}$alkyl, $SO_2NH_2$, $SO_2NHC_{1-6}$alkyl, and $SC_{1-4}$alkyl. More particularly, in another embodiment of the invention, the optional substituents on $R^1$ and $R^2$ in the compounds of the formulae Ia, Ib and II are independently selected from OH, F, Cl, Br, CN, $NO_2$, phenyl and $C_{1-4}$alkyl. Still more particularly, the optional substituents on $R^1$ and $R^2$ in the compounds of the formulae Ia, Ib and II further comprise at least one stereocenter.

It is an embodiment of the invention that $R^3$ to $R^7$ in the compounds of the formulae Ia, Ib and III are independently selected from H, $C_{1-10}$alkyl, $C_{3-12}$cycloalkyl, aryl and heteroaryl, the latter 4 groups being optionally substituted. In another embodiment of the invention, one or more of the carbons in $C_{1-10}$alkyl and $C_{3-10}$cycloalkyl is optionally replaced with a heteromoiety selected from O, S, N, $NR^{10}$ and $NR^{10}R^{11}$ in which $R^{10}$ and $R^{11}$ are independently selected from H and $C_{1-6}$alkyl. In a particular embodiment of the invention, $R^3$ to $R^7$ in the compounds of the formulae Ia, Ib and III are independently selected from H and $C_{1-6}$alkyl. In a more particular embodiment of the invention, $R^3$ to $R^7$ in the compounds of the formulae Ia, Ib and III are independently selected from H and methyl. Still further, in an embodiment of the invention, the optional substituents on $R^3$ and $R^7$ in the compounds of the formulae Ia, Ib and III are independently selected from OH, halo, CN, $NO_2$, phenyl, benzyl, $OC_{1-6}$alkoxy, $C_{1-6}$alkyl, $C_{1-6}$alkenyl, $C_{1-6}$alkenyloxy, $NH_2$, $NH(C_{1-6}alkyl)$, $N(C_{1-6}alkyl)(C_{1-6}alkyl)$, $C(O)C_{1-6}$alkyl, $C(O)OC_{1-6}$alkyl, $SO_2C_{1-6}$alkyl, $SO_2NH_2$, $SO_2NHC_{1-6}$alkyl, and $SC_{1-4}$alkyl.

It is an embodiment of the invention that $R^3$ and $R^9$ in the compound of the formula III are independently selected from H, $C_{1-10}$alkyl, $C_{3-12}$cycloalkyl, aryl and heteroaryl, the latter 4 groups being optionally substituted. In a more particular embodiment of the invention, $R^8$ and $R^9$ in the compound of the formula III are independently selected from H or $C_{1-6}$alkyl. In another embodiment of the invention, $R^8$ and $R^9$ in the compound of the formula III are linked to form an optionally substituted monocyclic or polycyclic ring system having 5 to 12 atoms, including the B and O atoms to which $R^8$ and $R^9$ are bonded. In a more particular embodiment of the invention, $R^8$ and $R^9$ in the compound of the formula III are linked to form an optionally substituted monocyclic or bicyclic ring system having 5 to 12 atoms, including the B and O atoms to which $R^8$ and $R^9$ are bonded. It is an embodiment of the invention that the optional substituents on $R^8$ and $R^9$ in the compound of the formula III are independently selected from OH, halo, CN, $NO_2$, phenyl, benzyl, $OC_{1-6}$alkoxy, $C_{1-6}$alkyl, $C_{1-6}$alkenyl, $C_{1-6}$alkenyloxy, $NH_2$, $NH(C_{1-6}alkyl)$, $N(C_{1-6}alkyl)(C_{1-6}alkyl)$, $C(O)C_{1-6}$alkyl, $C(O)OC_{1-6}$alkyl, $SO_2C_{1-6}$alkyl, $SO_2NH_2$, $SO_2NHC_{1-6}$alkyl, and $SC_{1-4}$alkyl. Still further, it is an embodiment of the invention that the optional substituent on $R^8$ and $R^9$ in the compound of the formula III is $C_{1-4}$alkyl.

In an embodiment of the invention, the method is performed in the presence of ammonia. In yet another embodiment of the invention, the method is performed in the presence of an ammonia salt $NH_3^+X^-$ in which X is an anionic ligand. In a further embodiment of the invention, X is selected from halo, $R^{12}COO$, $R^{12}SO_4$ and $BF_4$ in which $R^{12}$ is selected from $C_{1-10}$alkyl, $C_{3-20}$cycloalkyl, aryl and heteroaryl, all of which are optionally substituted. In an embodiment of the invention, X is selected from Cl, Br, $R^{12}COO$, $R^{12}SO_4$ and $BF_4$ and in which $R^{12}$ is selected from $C_{1-4}$alkyl, $C_{3-12}$cycloalkyl, aryl and heteroaryl, all of which are optionally substituted. In a still further embodiment of the invention, the optional substituents on $R^{12}$ are independently selected from OH, halo, CN, $NO_2$, phenyl, benzyl, $OC_{1-6}$alkoxy, $C_{1-6}$alkyl, $C_{1-6}$alkenyl, $C_{1-6}$alkenyloxy, $NH_2$, $NH(C_{1-6}$alkyl$)$, $N(C_{1-6}$alkyl$)(C_{1-6}$alkyl$)$, $C(O)C_{1-6}$alkyl, $C(O)OC_{1-6}$alkyl, $SO_2C_{1-6}$alkyl, $SO_2NH_2$, $SO_2NHC_{1-6}$alkyl, and $SC_{1-4}$alkyl.

In an embodiment of the invention, the method is performed in an inert organic solvent. More particularly, the organic solvent is selected from methanol, ethanol, propanol, butanol, toluene, tetrahydrofuran, acetonitrile, benzene, methylene chloride. Still more particularly, the organic solvent is methanol.

Also within the scope of the invention, the method is performed at room temperature or above or below room temperature for example at a temperature of from −40° C. to 100° C., suitably 0° C. to 50° C. more suitably 10° C. to 30° C. Suitably, the method is performed at room temperature. A person skilled in the art would appreciate that the reaction temperature may vary depending on a number of variables, including, but not limited to the structure of the starting materials (compounds of formulae II and III), the solvent, reaction pressure and the choice of ammonia or ammonia equivalent. A person skilled in the art would be able to optimize the reaction temperature to obtain the best yields and overall performance of the reaction.

Although there are a number of methods which have been surveyed to synthesize and isolate N-unsubstituted ketimines of the compound of the formula IV [P. L. Pickard and T. L. Tolbert, J. Org. Chem., 1961, 26, 4886; D. R. Boyd, K. M. McCombe and N. D. Sharma, Tetrahedron Lett., 1982, 23, 2907; A. J. Bailey and B. R. James, Chem. Commun., 1996, 2343; Y. Bergman, P. Perlmutter and N. Thienthong, Green Chem., 2004, 6, 539; and R. W. Layer, Chem. Rev., 1963, 63, 489], the present inventors have found that the three-component reaction of the ketone of the compound of the formula II, excess ammonia and the allylorganometallic of the compound of the formula III was the most efficient and effective protocol to generate the desired homoallylic amines of the compounds of formulae Ia and Ib (Scheme I).

Scheme I

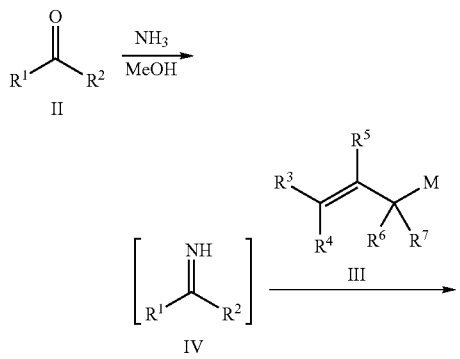

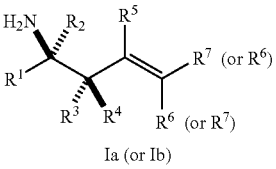

Ia (or Ib)

While not wishing to be limited by theory, it is believed that the N-unsubstituted ketimine of the compound of formula IV is formed in situ prior to its reaction with the allylorganometallic of the compound of formula III [M. Sugiura, K. Hirano and S. Kobayashi, J. Am. Chem. Soc., 2004, 126, 7182; S. Kobayashi, K. Hirano, M. Sugiura, Chem. Commun., 2005, 104; B. Davis, J. Labelled Compd. Radiopharm., 1987, 24, 1221; and N. Haider, G. Heinisch, I. Kurzmann-Rauscher and M. Wolf, Liebigs Ann. Chem., 1985, 167]. The addition of a series of allyl organometallics to the in situ generated ketimine of the compound of formula IV ($R^1$=4-$BrC_6H_4$, $R^2$=Me) have been investigated.

The following non-limiting examples are illustrative of the present invention:

EXAMPLES

Materials and Methods

All ketones in liquid form were distilled prior to use. All ketones in solid form were used as received. All other reagents were used as received (Aldrich, Acros, Strem). MeOH was dried over magnesium methoxide and distilled prior to use. 2 M solutions of allyl, (E)- and (Z)-crotylboronic acid in anhydrous MeOH were prepared just prior to use (exact molarities were confirmed by titration with benzaldehyde) [H. C. Brown, U.S. Racherla and P. J. Pellechia, J. Org. Chem., 1990, 55, 1868].

Melting points were uncorrected and were measured on a Fisher-Johns melting point apparatus. $^1H$ and $^{13}C$ NMR were recorded at 300 or 500 MHz and 75 or 125 MHz respectively on a Bruker Spectrospin 300 or 500 MHz spectrometer. Proton chemical shifts were internally referenced to the residual proton resonance in $CDCl_3$ (δ 7.26). Carbon chemical shifts were internally referenced to the deuterated solvent signals in $CDCl_3$ (δ 77.00). Infrared spectra were obtained on a Bruker VECTOR22 FT-IR spectrometer. HRMS-Cl and HRMS-ESI were performed on a Waters/Micromass GCT time-of-flight mass spectrometer and a Waters/Micromass Q-TOF Global quadrupole time-of-flight mass spectrometer respectively.

Example 1

General Procedure for the Allylation of N-Unsubstituted Imines Derived from Ketones To the ketone (0.5 mmol) was added a solution of ammonia in methanol (ca. 7M in MeOH, 0.75 mL, ca. 10 equiv.). The resulting solution was stirred for 15 min at rt. A freshly prepared solution of allylboronic acid (5e) (2M in MeOH, 0.4 ml, 0.8 mmol) was then added dropwise over 5 min. The reaction mixture was subsequently stirred for 16 h at rt. All volatiles were removed in vacuo and the residue re-dissolved in $Et_2O$ (15 mL). The desired amine was then extracted with 1 N HCl (15 ml). The acidic aqueous extract was washed with $Et_2O$ (3×15 mL). The aqueous extract was next made alkaline by addition of solid NaOH (ca. 5 g). The alkaline aqueous layer was then extracted with dichloromethane (3×15 mL).

The combined organic extracts were dried (Na$_2$SO$_4$), filtered and concentrated in vacuo to afford the desired tertiary carbamine (6).

(i) 1-(4-Bromophenyl)-1-methylbut-3-enylamine (6a)

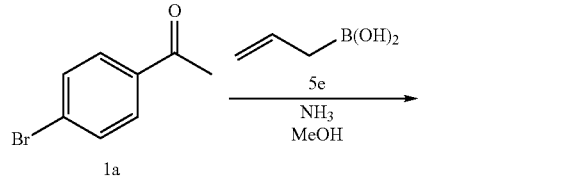

6a was isolated as a clear, colorless oil: $^1$H NMR (CDCl$_3$, 500 MHz) δ 7.44 (2H, d, J=8.5 Hz), 7.35 (2H, d, J=8.5 Hz), 5.55 (1H, dddd, J=18.0, 9.5, 8.0, 7.0 Hz), 5.09-5.04 (2H, m), 2.53 (1H, dd, J=13.5, 7.0 Hz), 2.38 (1H, dd, J=13.5, 8.0 Hz), 1.49 (2H, br s), 1.44 (3H, s); $^{13}$C NMR (CDCl$_3$, 125 MHz) δ 147.79, 133.89, 131.14, 127.26, 120.12, 118.81, 54.45, 49.64, 30.93; IR (film) υ3423, 1638 cm$^{-1}$; HRMS (CI) m/z calcd. for C$_{11}$H$_{15}$BrN (MH$^+$) 240.0388, found 240.0395.

(ii) 1,1-Diethylbut-3-enylamine (6b)

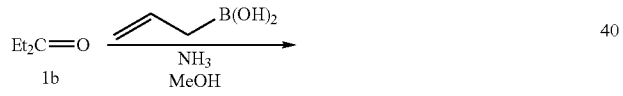

6b was isolated as a clear, colorless oil: $^1$H NMR (CDCl$_3$, 300 MHz) δ 5.77 (1H, ddt, J=16.0, 11.0, 7.5 Hz)), 5.04 (1H, d, J=11.0 Hz), 5.03 (1H, d, J=16.0 Hz), 2.03 (2H, d, J=7.5 Hz), 1.32 (4H, q, J=7.5 Hz), 1.18 (2H, br s), 0.81 (6H, t, J=7.5 Hz); $^{13}$C NMR (CDCl$_3$, 75 MHz) δ 134.44, 117.69, 53.36, 43.85, 31.66, 7.70; IR (film) v 3420, 1636 cm$^{-1}$; HRMS (ESI) m/z calcd. for C$_8$H$_{18}$N (MH$^+$) 128.1439, found 128.1444.

(iii) 2-Amino-2-methylpent-4-en-1-ol (6c)

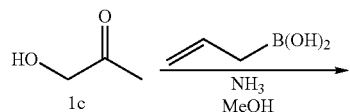

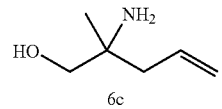

6c was isolated as a clear, colorless oil: $^1$H NMR (CDCl$_3$, 300 MHz) δ 5.79 (1H, ddt, J=16.5, 10.5, 7.5 Hz), 5.12-5.01 (2H, m), 3.30 (1H, d, J=10.5 Hz), 3.25 (1H, d, J=10.5 Hz), 2.45 (3H, br s), 2.11 (2H, d, J=7.5 Hz), 1.01 (3H, s); $^{13}$C NMR (CDCl$_3$, 75 MHz) δ 133.77, 118.51, 68.07, 52.70, 44.28, 24.53; IR (film) v 0.3345, 3157, 1639 cm$^{-1}$; HRMS (CI) m/z calcd. for C$_6$H$_{14}$NO (MH$^+$) 116.1075, found 116.1072.

(iv) 1-Benzyl-1-phenylbut-3-enylamine (6d)

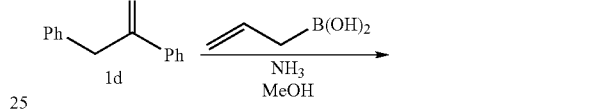

6d was isolated as a clear, colorless oil: $^1$H NMR (CDCl$_3$, 300 MHz) δ 7.38-7.08 (8H, m), 6.90-6.84 (2H, m), 5.53 (1H, dddd, J=17.0, 10.0, 8.5, 5.5 Hz), 5.15-5.00 (2H, m), 3.12 (1H, d, J=13.0 Hz), 2.97 (1H, d, J=13.0 Hz), 2.86 (1H, dd, J=13.5, 5.5 Hz), 2.44 (1H, dd, J=13.5, 8.5 Hz), 1.50 (2H, brs); $^{13}$C NMR (CDCl$_3$, 75 MHz) δ 146.52, 137.09, 134.08, 130.68, 128.07, 127.86, 126.46, 126.30, 126.19, 118.81, 57.97, 50.54, 47.62; IR (film) υ3401, 1677 cm$^{-1}$; HRMS (ESI) m/z calcd. for C$_{17}$H$_{20}$N (MH$^+$) 238.1596, found 238.1585.

(v) 1-Methyl-1-(3-methylbutyl)but-3-enylamine (6e)

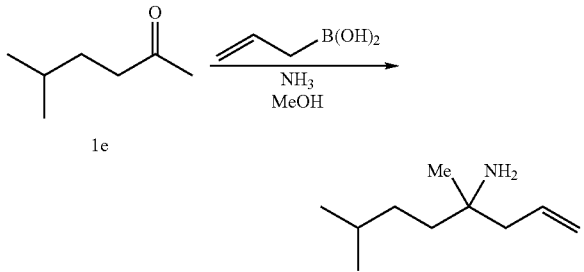

6e was isolated as a clear, colorless oil: $^1$H NMR (CDCl$_3$, 300 MHz) δ 5.74 (1H, ddt, J=17.0, 10.0, 7.5 Hz), 5.05-4.93 (2H, m), 2.00 (2H, d, J=7.5 Hz), 1.40 (1H, septet, J=6.5 Hz), 1.29-1.20 (2H, m), 1.19-1.03 (4H, m), 0.95 (3H, s), 0.80 (6H, d, J=6.5 Hz); $^{13}$C NMR (CDCl$_3$, 75 MHz) δ 134.50, 117.77, 51.14, 47.15, 40.36, 32.82, 28.45, 27.71, 22.53; IR (film) υ3385, 1636 cm$^{-1}$; HRMS (ESI) m/z calcd. for C$_{10}$H$_{22}$N (MH$^+$) 156.1752, found 156.1745.

(vi) 1-Ethyl-1-(4-Methoxyphenyl)but-3-enylamine (6f)

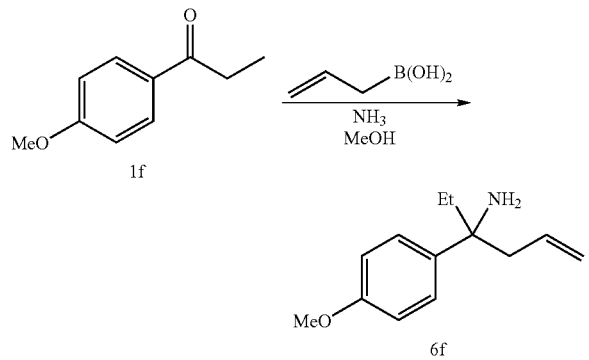

6f was isolated as a clear, colorless oil: $^1$H NMR (CDCl$_3$, 500 MHz) δ 7.31 (2H, d, J=9.0 Hz), 6.86 (2H, d, J=9.0 Hz), 5.53 (1H, dddd, J=17.5, 10.0, 8.5, 6.0 Hz), 5.06 (1H, d, J=17.5 Hz), 5.03 (1H, d, J=10.0 Hz), 3.80 (3H, s), 2.59 (1H, dd, J=13.5, 6.0 Hz), 2.36 (1H, dd, J=13.5, 8.5 Hz), 1.85 (1H, dq, J=14.0, 7.5 Hz), 1.66 (1H, dq, J=14.0, 7.5 Hz), 1.52 (2H, br s), 0.71 (3H, t, J=7.5 Hz); $^{13}$C NMR (CDCl$_3$, 75 MHz) δ 157.72, 138.66, 134.32, 126.93, 118.34, 113.27, 57.06, 55.16, 48.37, 36.05, 8.04; IR (film) υ3420, 1638, 1610, 1511, 1248 cm$^{-1}$; HRMS (CI) m/z calcd. for C$_{13}$H$_{20}$NO (MH$^+$) 206.1545, found 206.1565.

(vii) 4-(1-Amino-1-methylbut-3-enyl)benzonitrile (6g)

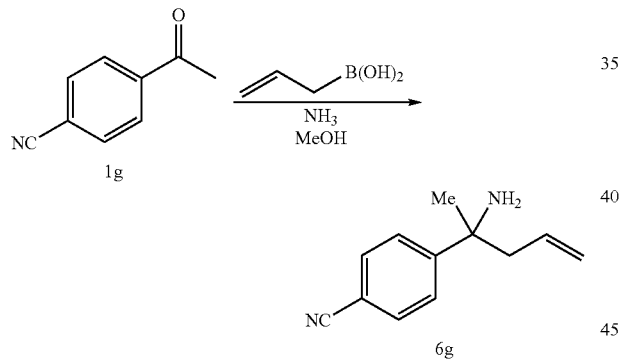

6g was isolated as a clear, colorless oil: $^1$H NMR (CDCl$_3$, 300 MHz) δ 7.57 (4H, apparent s), 5.55-5.40 (1H, m), 5.07-4.97 (2H, m), 2.51 (1H, dd, J=13.5, 6.5 Hz), 2.36 (1H, dd, J=13.5, 8.0 Hz), 1.46 (2H, br s), 1.43 (3H, s); $^{13}$C NMR (CDCl$_3$, 75 MHz) δ 154.26, 133.32, 131.99, 126.36, 119.37, 119.03, 110.05, 54.94, 49.50, 30.85; IR (film) υ3499, 2228, 1639 cm$^{-1}$; HRMS (CI) m/z calcd. for C$_{12}$H$_{15}$N$_2$ (MH$^+$) 187.1235, found 187.1235.

(viii) 1-Methyl-1-(4-nitrophenyl)but-3-enylamine (6h)

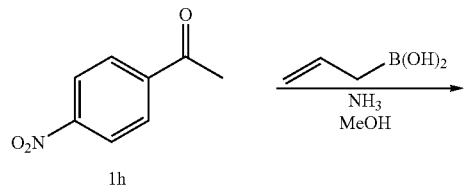

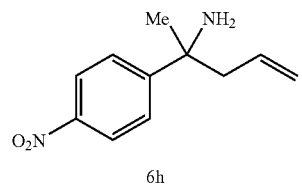

6h was isolated as a clear, colorless oil: $^1$H NMR (CDCl$_3$, 500 MHz) δ 8.16 (2H, d, J=9.0 Hz), 7.66 (2H, d, J=9.0 Hz), 5.53 (1H, dddd, J=17.0, 10.5, 8.0, 7.0 Hz), 5.07 (1H, d, J=10.5 Hz), 5.06 (1H, d, J=17.0 Hz), 2.57 (1H, dd, J=13.5, 7.0 Hz), 2.42 (1H, dd, J=13.5, 8.0 Hz), 1.54 (2H, br s), 1.50 (3H, s); $^{13}$C NMR (CDCl$_3$, 125 MHz) δ 156.28, 146.47, 133.13, 126.45, 123.30, 119.43, 55.01, 49.55, 30.92; IR (film) v3375, 1639, 1526, 1351 cm$^{-1}$; HRMS (CI) m/z calcd. for C$_{11}$H$_{15}$N$_2$O$_2$ (MH$^+$) 207.1134, found 207.1132.

(ix) 1-Methyl-1E-styrylbut-3-enylamine (6i)

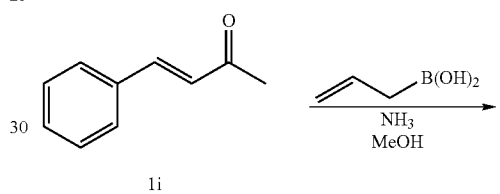

6i was isolated as a clear, colorless oil: $^1$H NMR (CDCl$_3$, 300 MHz) δ 7.45-7.15 (5H, m), 6.46 (1H, d, J=16.0 Hz), 6.28 (1H, d, J=16.0 Hz), 5.87-5.72 (1H, m), 5.18-5.05 (2H, m), 2.31 (1H, dd, J=16.5, 7.5 Hz), 2.23 (1H, dd, J=16.5, 8.0 Hz), 1.41 (2H, br s), 1.27 (3H, s); $^{13}$C NMR (CDCl$_3$, 75 MHz) δ 138.42, 137.22, 133.95, 128.39, 128.27, 127.06, 126.14, 118.45, 52.96, 48.00, 28.57; IR (film) v 3545, 1638 cm$^{-1}$; HRMS (CI) m/z calcd. for C$_{13}$H$_{18}$N (MH$^+$) 118.1439, found 118.1449.

(x) 9-Allyl-9H-fluoren-9-ylamine (6j)

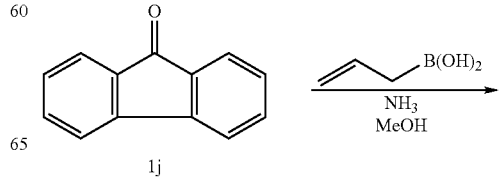

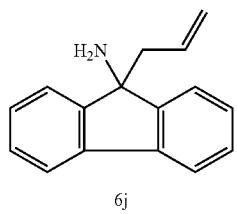

6j

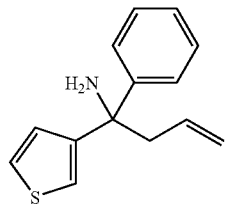

6l 6j was isolated as a clear, colorless oil: $^1$H NMR (CDCl$_3$, 500 MHz) δ 7.66 (2H, d, J=7.5 Hz), 7.51 (2H, d, J=7.0 Hz), 7.38-7.30 (4H, m), 5.57 (1H, ddt, J=17.0, 10.0, 7.5 Hz), 5.01 (1H, dd, J=17.0, 1.5 Hz), 4.96 (1H, d, J=10.0 Hz), 2.70 (2H, d, J=7.5 Hz), 1.81 (2H, br s); $^{13}$C NMR (CDCl$_3$, 125 MHz) δ 150.86, 139.28, 133.22, 128.00, 127.53, 123.26, 119.85, 118.60, 64.71, 45.46; IR (film) ν3360, 1640 cm$^{-1}$; HRMS (ESI) m/z calcd. for C$_{16}$H$_{16}$N (MH$^+$) 222.1283, found 222.1278.

6l was isolated as a clear, colorless oil: $^1$H NMR (CDCl$_3$, 500 MHz) δ 7.49 (2H, dt, J=7.5, 1.0 Hz), 7.33 (2H, t, J=8.0 Hz), 7.27-7.17 (2H, m), 6.94 (1H, dd, J=5.0, 3.5 Hz), 6.90 (1H, dd, J=3.5, 1.0 Hz), 5.62 (1H, ddt, J=17.0, 10.0, 7.0 Hz), 5.19 (1H, d, J=17.0, 1.5 Hz), 5.13 (1H, ddd, J=10.0, 1.5, 1.0 Hz), 3.08 (1H, dd, J=14.0, 7.0 Hz), 3.01 (1H, dd, J=14.0, 7.5 Hz), 2.09 (2H, br s); $^{13}$C NMR (CDCl$_3$, 75 MHz) δ 154.78, 147.10, 133.63, 128.15, 126.77, 126.50, 126.01, 124.22, 123.64, 119.55, 59.32, 49.15; IR (film) ν3410, 1639 cm$^{-1}$; HRMS (CI) m/z calcd. for C$_{14}$H$_{16}$NS (MH$^+$) 230.1003, found 230.1017.

(xi) 4-Allyl-1-benzylpiperidin-4-ylamine (6k)

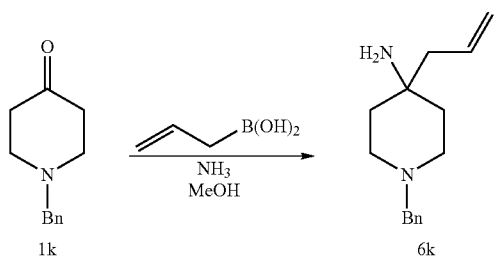

6k was isolated as a clear, colorless oil: $^1$H NMR (CDCl$_3$, 300 MHz) δ 7.32-7.15 (5H, m), 5.81 (1H, ddt, J=17.0, 10.0, 7.5 Hz), 5.12-5.01 (2H, m), 3.48 (2H, s), 2.58-2.48 (2H, dq, J=12.0, 4.0 Hz), 2.30 (2H, dt, J=11.0, 3.0 Hz), 2.09 (2H, d, J=7.5 Hz), 1.61 (2H, ddd, J=13.0, 10.5, 4.0 Hz), 1.41-1.31 (2H, m), 1.08 (2H, br s); $^{13}$C NMR (CDCl$_3$, 75 MHz) δ 138.43, 133.51, 128.88, 127.95, 126.69, 118.29, 63.08, 49.39, 48.67, 47.60, 37.83; IR (film) ν3422, 1639 cm$^{-1}$; HRMS (ESI) m/z calcd. for C$_{15}$H$_{23}$N$_2$ (MH$^+$) 231.1861, found 231.1862.

(xii) 1-Phenyl-1-thiophen-2-ylbut-3-enylamine (6l)

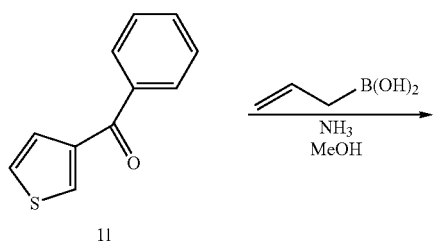

(xiii) 1-(1H-Indol-3-yl)-1-methylbut-3-enylamine (6m)

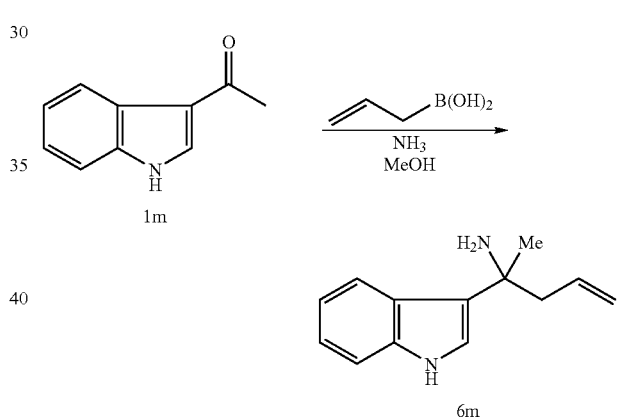

6m was isolated as a clear, colorless oil: $^1$H NMR (CDCl$_3$, 500 MHz) δ 8.03 (1H, br s), 7.84 (1H, d, J=8.0 Hz), 7.37 (1H, d, J=8.0 Hz), 7.19 (1H, dt, J=7.5, 1.0 Hz), 7.12 (1H, dt, J=7.5, 1.0 Hz), 7.07 (1H, d, J=2.5 Hz), 5.65 (1H, ddt, J=17.5, 10.0, 7.5 Hz), 5.06 (1H, d, J=17.5 Hz), 5.03 (1H, d, J=10.0 Hz), 2.79 (1H, dd, J=13.5, 7.5 Hz), 2.63 (1H, dd, J=13.5, 7.5 Hz), 1.85 (2H, br s), 1.61 (3H, s); $^{13}$C NMR (CDCl$_3$, 75 MHz) δ 137.30, 134.93, 125.20, 124.74, 121.77, 120.91, 120.51, 119.21, 117.92, 111.35, 52.39, 48.20, 30.00; IR (film) ν3205, 1639 cm$^{-1}$.

(xiv) 1-Allyl-4-tert-butylcyclohexylamine (6n)

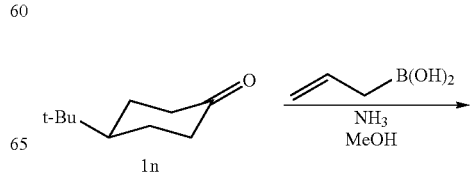

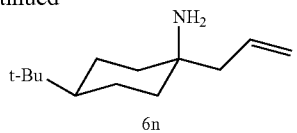

6n was isolated as a clear, colorless oil (d.r.=87:13). The diastereomeric ratio was determined by $^1$H NMR of the crude sample. Main diastereomer: $^1$H NMR (CDCl$_3$, 300 MHz) δ 5.83 (1H, ddt, J=17.0, 10.5, 7.5 Hz), 5.08-4.98 (2H, m), 2.02 (2H, d, J=7.5 Hz), 1.60-1.40 (4H, m), 1.34-1.00 (6H, m), 0.90-0.83 (1H, m), 0.83 (9H, s); $^{13}$C NMR (CDCl$_3$, 75 MHz) δ 134.26, 117.87, 50.16, 49.94, 48.11, 38.43, 32.30, 27.50, 22.42; IR (film) υ3368, 1638 cm$^{-1}$; HRMS (CI) m/z calcd. for C$_{13}$H$_{26}$N (MH$^+$) 196.2065, found 196.2068. The stereochemistry of 6n (axial NH$_2$) was confirmed by converting it (allylbromide, iPr$_2$NEt, CH$_2$Cl$_2$; 49%) to the previously known compound N-Allyl-1-Allyl-4-tert-butylcyclohexylamine (axial NHCH$_2$CH=CH) [D. L. Wright, J. P. Schulte, II and M. A. Page, Org. Lett., 2000, 2, 1847].

(xv) 2-Allyl-bicyclo[2.2.1]hept-2-ylamine (6o)

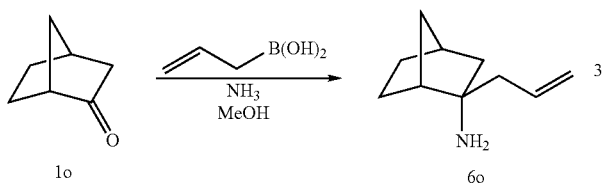

6o was isolated as a clear, colorless oil (d.r.=94:6). The diastereomeric ratio was determined by $^1$H NMR of the crude sample. Main diastereomer: $^1$H NMR (CDCl$_3$, 300 MHz) δ 5.78 (1H, ddt, J=17.0, 10.5, 7.5 Hz), 5.08-4.97 (2H, m), 2.10 (2H, d, J=7.5 Hz), 1.88 (1H, d, J=3.5 Hz), 1.78 (1H, ddt, J=12.5, 9.0, 3.0 Hz), 1.60-1.42 (3H, m), 1.24-1.08 (6H, m), 0.82 (1H, dd, J=12.5, 3.0 Hz); $^{13}$C NMR (CDCl$_3$, 75 MHz) δ 134.57, 117.95, 57.99, 47.41, 46.69, 46.48, 38.30, 37.54, 28.43, 22.92; IR (film) υ3400, 1638 cm$^{-1}$; HRMS (CI) m/z calcd. for C$_{10}$H$_{18}$N (MH$^+$) 152.1439, found 152.1435.

(xvi) 2-Amino-1,2-diphenylpent-4-en-1-ol (6p)

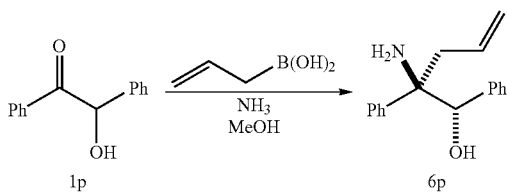

6p was isolated as a clear, colorless crystalline solid. The diastereomeric ratio (d.r.=88:12) was determined by $^1$H NMR of the crude sample. Main diastereomer: m.p.=85-86° C. (CH$_2$Cl$_2$); $^1$H NMR (CDCl$_3$, 300 MHz) δ 7.30-7.06 (8H, m), 6.90-6.85 (2H, m), 5.56-5.40 (1H, m), 5.12 (1H, d, J=17.0 Hz), 5.00 (1H, d, J=10.0 Hz), 4.74 (1H, s), 2.95 (1H, dd, J=14.0, 5.5 Hz), 2.65 (1H, dd, J=14.0, 9.0 Hz), 2.08 (3H, br s); $^{13}$C NMR (CDCl$_3$, 75 MHz) δ142.54, 140.02, 133.74, 127.62, 127.42, 127.24, 127.10, 126.71, 126.50, 118.96, 79.91, 61.70, 43.45; IR (film) υ3422, 1638 cm$^{-1}$; HRMS (CI) m/z calcd. for C$_{17}$H$_{20}$NO (MH$^+$) 254.1545, found 254.1543.

(xvii) (1S*,2R*,5R*)-2-Allyl-4,6,6-trimethylbicyclo[3.1.1]hept-3-en-2-ylamine (6q)

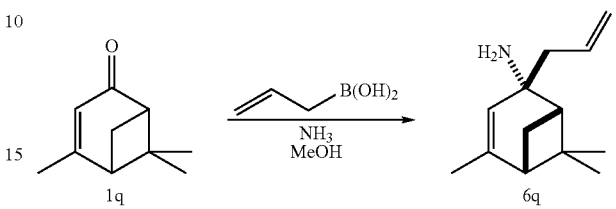

6q was isolated as a clear, colorless oil (d.r.=97:3). The diastereomeric ratio was determined by $^1$H NMR of the crude sample. $^1$H NMR (CDCl$_3$, 300 MHz) δ 5.85 (1H, ddt, J=17.5, 10.5, 7.5 Hz), 5.13-5.02 (3H, m), 2.36 (1H, dt, J=9.0, 5.5 Hz), 2.20 (1H, dd, J=13.5, 7.0 Hz), 2.13 (1H, dd, J=13.5, 8.0 Hz), 1.98-1.88 (2H, m), 1.68 (3H, d, J=1.5 Hz), 1.60-1.35 (3H, m), 1.33 (3H, s), 1.05 (3H, s); $^{13}$C NMR (CDCl$_3$, 75 MHz) δ 143.51, 133.89, 124.42, 118.23, 57.24, 52.84, 47.64, 45.88, 41.87, 33.78, 27.36, 23.85, 22.77; IR (film) υ3410, 1713, 1681, 1623 cm$^{-1}$; HRMS (ESI) m/z calcd. for C$_{13}$H$_{22}$N (MH$^+$) 192.1752, found 192.1756.

Example 2

Results for the Allylation of N-Unsubstituted Imines Derived from Ketones

The allylboron class of reagents were demonstrably superior in terms of reactivity and chemoselectivity [W. R. Roush, in Houben-Weyl, Stereoselective Synthesis, ed. G. Helmchen, R. W. Hoffmann, J. Mulzer and E. Schaumann, Georg Thieme Verlag, Stuttgart, 1995, vol. E21b, pp 1410-1486; D. S. Matteson, in Stereodirected Synthesis with Organoboranes, Springer-Verlag, Berlin, 1995]. In order to ascertain the reagent of choice, the present inventors have investigated the addition of a range of allylboron compounds to N-unsubstituted ketimines which are derived from ketones. The results are shown in Table 1. As can be seen from the Table, the more reactive allylboron reagents, 5d and 5e [H. C. Brown, U.S. Racherla and P. J. Pellechia, J. Org. Chem., 1990, 55, 1868] displayed the highest efficacy in terms of isolated yields of homollylic amine 6a (entries 4 and 5). A major issue of concern in all these reactions—chemoselectivity of imine versus ketone addition—was addressed by analyzing the organic extracts from the acid-base workup of 6a (entries 4, 5). It was determined that the corresponding homoallylic alcohol of 6a was formed in minor amounts (≦5%).

Due to the ease of the preparation of the allylboron reagent 5e and the simple purification of the resulting products, the present inventors have further investigated a series of ketones with reagent 5e in methanolic ammonia (Table 2). Aliphatic (entries 1-4), electron rich aromatic (entry 5), electron deficient aromatic (entries 6 and 7), α,β-unsaturated (entry 8), cyclic (entries 9 and 10) and heterocyclic-substituted (entries 11 and 12) ketones were successfully allylated under the standard conditions. The resulting homoallylic amines (6) were easily isolated in high yields through simple acid-base extraction, and in all cases but one, did not require any further purification. A variety of functional groups were also found to be tolerated in the reaction sequence including the nitro (entry 7), cyano (entry 6), unprotected hydroxy (entry 2) and amino groups (entry 12).

Still further, the present inventors have expanded the scope of the study to include the allylation of ketones containing a pre-existing stereocenter. The substrates (1n-q) were subjected to the standard set of reaction and work-up conditions, the results of which are shown in Table 3. Good to excellent yields of tertiary carbinamines 6n-q were obtained in all cases, while the observed diastereoselectivities, as determined by $^1$H NMR, varied from modest for the reaction of 4-tert-butylcyclohexanone, norchamphor, and benzoin (equations 1, 2 and 3 respectively) to excellent for verbenone (equation 4).

Example 3

General Procedure for the Crotylation of N-Unsubstituted Imines Derived from Ketones The protocol for the allylation of N-unsubstituted imines derived from ketones was followed with the exception that the boron reagent was changed to either either (E)- or (Z)-crotylboronic acid (2M in MeOH, 0.5 mL, 1.00 mmol).

(i) (1S*,2S*)-1,2-Dimethyl-1-(4-trifluoromethylphenyl)but-3-enylamine (4a)

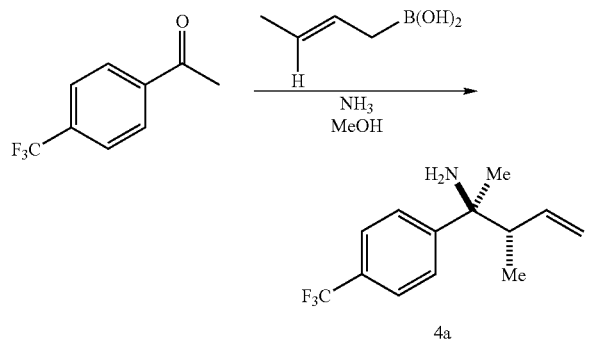

4a was isolated as a clear, colorless oil (d.r.=97:3). The diastereomeric ratio was determined by $^1$H NMR of the crude sample. $^1$H NMR (CDCl$_3$, 300 MHz) δ 7.60 (2H, d, J=9.0 Hz), 7.56 (2H, d, J=9.0 Hz), 5.66-5.53 (1H, m), 5.10-5.00 (2H, m), 2.53 (1H, pentet, J=7.0 Hz), 1.49 (2H, br s), 1.46 (3H, s), 0.91 (3H, d, J=7.0 Hz); $^{13}$C NMR (CDCl$_3$, 75 MHz) δ 152.45, 139.63, 128.52 (q, J=30 Hz), 126.37, 124.79 (q, J=3.5 Hz), 124.64 (q, J=270 Hz), 116.45, 55.96, 48.82, 27.13, 14.30; IR (film) ʋ3378, 1636 cm$^{-1}$; HRMS (ESI) m/z calcd. for C$_{13}$H$_{17}$F$_3$N (MH$^+$) 244.1313, found 244.1305.

(ii) (1S*,2R*)-1,2-Dimethyl-1-(4-trifluoromethylphenyl)but-3-enylamine (4b)

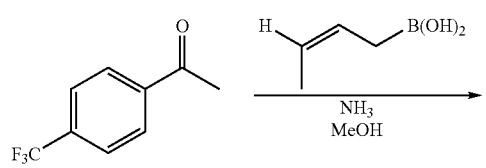

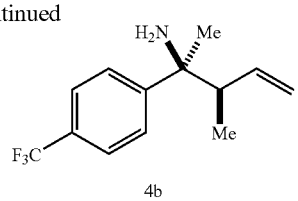

4b was isolated as a clear, colorless oil (d.r.=96:4). The diastereomeric ratio was determined by $^1$H NMR of the crude sample. $^1$H NMR (CDCl$_3$, 300 MHz) δ 7.56 (4H, apparent s), 5.75 (1H, ddd, J=18.5, 10.5, 8.0 Hz), 5.13-5.03 (2H, m), 2.53 (1H, pentet, J=7.5 Hz), 1.58 (2H, br s), 1.43 (3H, s), 0.78 (3H, d, J=7.5 Hz); $^{13}$C NMR (CDCl$_3$, 75 MHz) δ 152.10, 139.46, 128.02 (q, J=30 Hz), 126.23, 125.83 (q, J=270 Hz), 124.73 (q, J=3.5 Hz), 116.34, 55.56, 48.65, 29.51, 14.51; IR (film) ʋ3390, 1637 cm$^{-1}$; HRMS (ESI) m/z calcd. for C$_{13}$H$_{17}$F$_3$N (MH$^+$) 244.1313, found 244.1304.

(iii) (2S*,3S*)-2-Amino-3-methyl-2-phenylpent-4-enoic acid amide (4c)

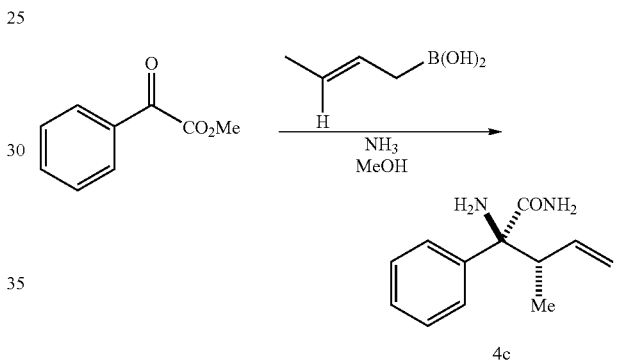

4c was isolated as a clear, colorless, crystalline solid (d.r.=97:3): m.p=90° C. (CH$_2$Cl$_2$); $^1$H NMR (CDCl$_3$, 300 MHz) δ 7.65-7.58 (2H, m), 7.35-7.18 (4H, m), 6.20 (1H, brs), 5.46 (1H, ddd, J=17.5, 10.0, 6.5 Hz), 5.05-4.95 (2H, m), 3.59 (1H, pentet, J=6.5 Hz), 1.59 (2H, br s), 1.08 (3H, d, J=6.5 Hz); $^{13}$C NMR (CDCl$_3$, 75 MHz) δ 176.99, 141.60, 138.23, 128.16, 127.04, 125.64, 116.69, 65.54, 42.58, 12.27; IR (film) ʋ3441, 3207, 1710, 1620, 1637 cm$^{-1}$; HRMS (CI) m/z calcd. for C$_{11}$H$_{17}$N$_2$O (MH$^+$) 205.1341, found 205.1332.

(iv) (2S*,3R*)-2-Amino-3-methyl-2-phenylpent-4-enoic acid amide (4d)

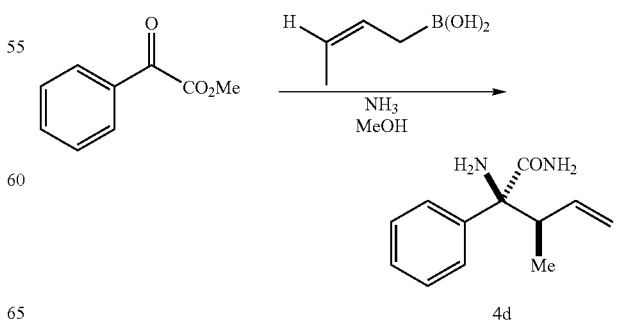

4d was isolated as a clear, colorless, crystalline solid (d.r.=96:4): m.p=136° C. (CH$_2$Cl$_2$); $^1$H NMR (CDCl$_3$, 500 MHz) δ 7.64-7.60 (2H, m), 7.35-7.24 (4H, m), 6.02 (1H, ddd, J=17.5, 10.5, 5.0 Hz), 5.59 (1H, br s), 5.26 (1H, dt, J=10.5, 1.5 Hz), 5.17 (1H, dt, J=17.5, 1.5 Hz), 3.76-3.69 (1H, m), 1.63 (2H, br s), 0.73 (3H, d, J=7.0 Hz); $^{13}$C NMR (CDCl$_3$, 125 MHz) δ 177.15, 141.16, 139.07, 128.24, 127.06, 125.54, 117.21, 65.47, 41.87, 10.97; IR (film) ν3432, 3170, 1715, 1633 cm$^{-1}$; HRMS (CI) m/z calcd. for C$_{11}$H$_{17}$N$_2$O (MH$^+$) 205.1341, found 205.1337.

(v) (1S*,2S*)-1,2-Dimethyl-1-phenylbut-3-enylamine (4e)

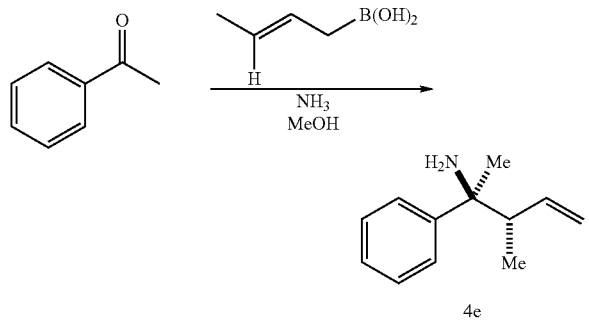

4e was isolated as a clear, colorless oil (d.r.=97:3). The diastereomeric ratio was determined by $^1$H NMR of the crude sample. $^1$H NMR (CDCl$_3$, 300 MHz) δ 7.42-7.10 (4H, m), 5.65-5.55 (1H, m), 4.96-5.02 (2H, m), 2.45 (1H, dq, J=7.0 Hz), 1.50 (2H, br s), 1.38 (3H, s), 0.83 (3H, d, J=7.0 Hz); $^{13}$C NMR (CDCl$_3$, 75 MHz) δ 148.22, 140.30, 127.87, 126.13, 125.79, 115.90, 56.81, 49.02, 26.68, 14.49 [C. Ogawa, M. Sugiura and S. Kobayashi, J. Org. Chem., 2002, 67, 5359].

(vi) 2-Amino-2,3-dimethylpent-4-enoicacid amide (4f)

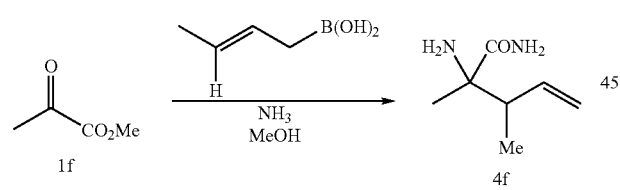

4f was isolated as a clear, colorless oil (d.r.=60:40). The diastereomeric ratio was determined by $^1$H NMR of the crude sample. Main diastereomer: $^1$H NMR (CDCl$_3$, 300 MHz) δ 7.41 (1H, br s), 5.95-5.60 (2H, m), 5.15-5.05 (2H, m), 2.81 (1H, pentet, J=6.5 Hz), 1.28 (3H, s), 1.26 (2H, br s), 0.99 (3H, d, J=6.5 Hz); $^{13}$C NMR (CDCl$_3$, 75 MHz) δ 180.06, 139.33, 116.28, 59.62, 43.29, 25.10, 11.88; IR (film) ν3444, 3250, 1691, 1654, 1557 cm$^{-1}$; HRMS (CI) m/z calcd. for C$_7$H$_{14}$N$_2$O (MH$^+$) 143.1184, found 143.1186.

Example 4

Results for the Crotylation of N-Unsubstituted Imines Derived from Ketones

The crotylation of a select number of ketones was examined under a slightly modified set of conditions (2.0 equiv of 5e, 10 equiv. of NH$_3$, rt, 24 h) (Table 4). Excellent diastereoselectivities were obtained with acetophenone derivatives (entries 1-4). The anti diastereomer (4a/c) was formed when (E)-crotylboronic acid (7a) was employed as the reagent, while (Z)-crotylboronic acid (7b) afforded the syn diastereomer (4b/d). The stereochemistry of the crotylated products 4 were assigned based upon the reaction of 7a with acetophenone (entry 5) which afforded the previously known anti diastereomer 4e in moderate yield and excellent diastereoselectivity (d.r.=97:3) [C. Ogawa, M. Sugiura and S. Kobayashi, J. Org. Chem., 2002, 67, 5359]. Crotylation of methyl pyruvate (entry 6), on the other hand, was not diastereoselective likely due to the similar steric sizes of the methyl and methylformate groups. The results from entries 3-5 also constitute a convenient route to α-allylated amino acid derivatives.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Addition of allyl boron reagents (5) to N-unsubstituted ketimine derived from 1a.

| Entry | 5 | Yield of 6a (%)$^a$ |
|---|---|---|
| 1 | (5a) | 35 |
| 2 | 5b | 29 |

TABLE 1-continued

Addition of allyl boron reagents (5) to N-unsubstituted ketimine derived from 1a.

[Scheme: 1a (4-bromoacetophenone) + allyl-BR₂ (5, 1.6 equiv.), NH₃ (ca. 10 equiv.), MeOH, rt, 16 h → 6a (2-(4-bromophenyl)-pent-4-en-2-amine)]

| Entry | 5 | Yield of 6a (%)[a] |
|---|---|---|
| 3 | allyl-B(O^iPr)₂ (5c) | 43 |
| 4 | allyl-B(catecholate) (5d) | 70[b,c] |
| 5 | allyl-B(OH)₂ (5e) | 79[b] |

[a] Isolated yield after acid-base extraction.
[b] Analysis (¹H NMR, 2,4,6-trimethylbenzene standard) of the organic phase from the acid-base work-up revealed ≦5% of the corresponding homoallylic alcohol.
[c] Isolated yield after acid-base extraction and preparative TLC.

TABLE 2

Reaction of N-unsubstituted imines derived from ketones with allylboronic acid (5e)[a].

[Scheme: R¹C(O)R² (1) + allyl-B(OH)₂ (5e, 1.6 equiv), NH₃ (10 equiv.), MeOH, rt, 16 h → R¹C(NH₂)(Me)CH₂CH=CH₂ (6)]

| Entry | Ketone | | Yield (%)[b] |
|---|---|---|---|
| 1 | Et₂C=O | (1b) | 73 (6b) |
| 2 | HOCH₂C(O)CH₃ | (1c) | 80 (6c) |
| 3 | PhCH₂C(O)Ph | (1d) | 78 (6d) |
| 4 | (iPr)CH₂CH₂C(O)CH₃ | (1e) | 85 (6e) |
| 5 | 4-MeOC₆H₄C(O)CH₂CH₃ | (1f) | 72 (6f) |
| 6 | 4-NCC₆H₄C(O)CH₃ | (1g) | 80 (6g) |
| 7 | 4-O₂NC₆H₄C(O)CH₃ | (1h) | 87 (6h) |
| 8 | PhCH=CHC(O)CH₃ | (1i) | 70 (6i)[c] |
| 9 | fluorenone | (1j) | 78 (6j) |
| 10 | 1-benzyl-4-piperidone | (1k) | 92 (6k) |
| 11 | 2-thienyl phenyl ketone | (1l) | 75 (6l) |
| 12 | 3-acetylindole | (1m) | 80 (6m) |

[a] Standard reaction conditions: A solution of the ketone (0.5 mmol), ammonia (ca. 7N in MeOH, 0.75 mL, ca. 10 equiv.) and allylboronic acid (5e) (2M in MeOH, 0.40 mL, 0.80 mmol) was stirred for 16 h at rt.
[b] Isolated yield after acid-base extraction.
[c] Isolated yield after acid-base extraction, and preparative TLC.

TABLE 3

Reaction of N-unsubstituted imines derived from ketones with allylboronic acid (5e) in which the ketones contain a pre-existing stereocentre.

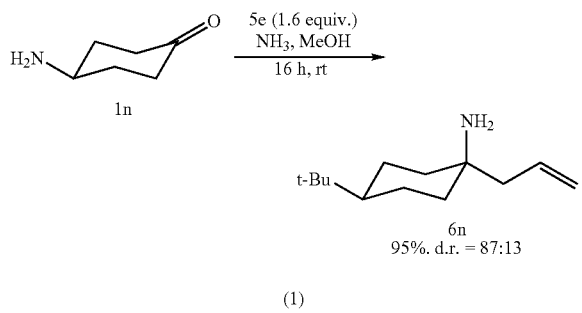

(1)

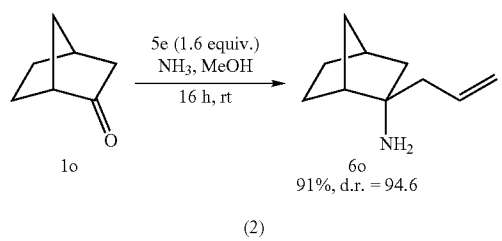

(2)

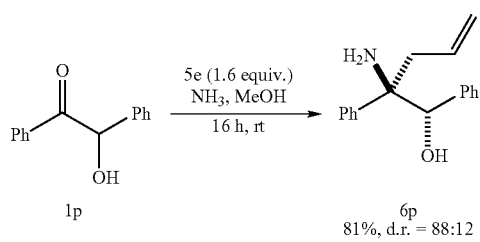

(3)

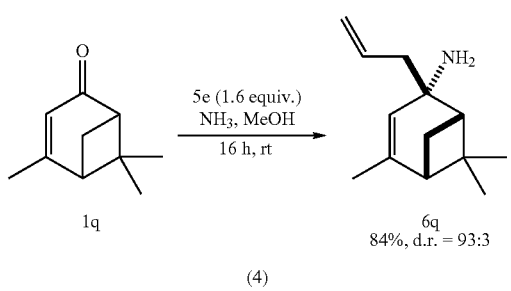

(4)

TABLE 4

Reaction of N-unsubstituted ketimines with (E)- and (Z)-crotylboronic acid (7a/b)[a]

| Entry | Crotyl reagent | Product | Yield (%)[b] | d.r. |
|---|---|---|---|---|
| 1 | 7a | (p-CF$_3$-C$_6$H$_4$)-C(NH$_2$)-CH(Me)-CH=CH$_2$ | 80 (4a) | 97:3 |
| 2 | 7b | (p-CF$_3$-C$_6$H$_4$)-C(NH$_2$)-CH(Me)-CH=CH$_2$ | 73 (4b)[c] | 96:4 |
| 3 | 7a | Ph-C(NH$_2$)(CONH$_2$)-CH(Me)-CH=CH$_2$ | 95 (4c)[d] | 97:3 |
| 4 | 7b | Ph-C(NH$_2$)(CONH$_2$)-CH(Me)-CH=CH$_2$ | 92 (4d)[d] | 96:4 |
| 5 | 7a | Ph-C(NH$_2$)(Me)-CH(Me)-CH=CH$_2$ | 50 (4e) | 97:3 |
| 6 | 7a | Me-C(NH$_2$)(CONH$_2$)-CH(Me)-CH=CH$_2$ | 88 (4f)[e] | 60:40 |

[a]Standard reaction conditions: ketone (0.5 mmol), ammonia (ca. 7N in MeOH, 0.75 mL, ca. 10 equiv.) and crotylboronic acid (7a/b) (2M in MeOH, 0.50 mL, 1.00 mmol) were stirred for 24 h at rt.
[b]Isolated yield after acid-base extraction.
[c]Isolated yield after acid-base extraction, and preparative TLC.
[d]Methyl benzoylformate was employed as the starting ketone, and aminolysis of the ester was observed.
[e]Methylpyruvate was employed as the starting ketone, and aminolysis of the ester was observed.

We claim:

1. A method of preparing an amine of the formula Ia and/or Ib comprising reacting a compound of formula II with a compound of formula III:

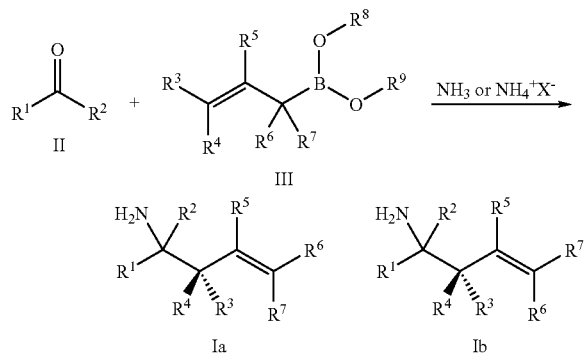

wherein $R^1$ and $R^2$ are independently selected from $C_{1-20}$alkyl, $C_{1-20}$alkoxy, $C_{2-20}$alkenyl, $C_{3-20}$cycloalkyl, $C_{3-20}$cycloalkoxy, aryl, aryloxy, heteroaryl and heteroaryloxy, all of which are optionally substituted and one or more of the carbons in $C_{1-20}$alkyl, $C_{1-20}$alkoxy, $C_{2-20}$alkenyl, $C_{3-20}$cycloalkyl and $C_{3-20}$cycloalkoxy, is optionally replaced with a heteromoiety selected from 0, S, N, $NR^{10}$ and $NR^{10}R^{11}$;

or $R^1$ and $R^2$ are linked to form an optionally substituted monocyclic or polycyclic ring system having 4 to 20 atoms including the carbonyl to which $R^1$ and $R^2$ are bonded, and one or more of the carbons of the ring system is optionally replaced with a heteromoiety selected from O, S, N, $NR^{10}$ and $NR^{10}R^{11}$;

$R^3$ to $R^7$ are independently selected from H, $C_{1-20}$alkyl, $C_{1-20}$alkoxy, $C_{2-20}$alkenyl, $C_{3-20}$cycloalkyl, $C_{3-20}$cycloalkoxy, aryl, aryloxy, heteroaryl and heteroaryloxy, the latter 9 groups being optionally substituted and one or more of the carbons in $C_{1-20}$alkyl, $C_{1-20}$alkoxy, $C_{2-20}$alkenyl, $C_{3-20}$cycloalkyl and $C_{3-20}$cycloalkoxy, is optionally replaced with a heteromoiety selected from O, S, N, $NR^{10}$ and $NR^{10}R^{11}$;

$R^8$ and $R^9$ are independently selected from H, $C_{1-20}$alkyl, $C_{3-20}$cycloalkyl, aryl and heteroaryl, the latter 4 groups being optionally substituted;

or $R^8$ and $R^9$ are linked to form an optionally substituted monocyclic or polycyclic ring system having 4 to 20 atoms, including the B and O atoms to which $R^8$ and $R^9$ are bonded;

$R^{10}$ and $R^{11}$ are independently selected from H, $C_{1-20}$alkyl, $C_{3-20}$cycloalkyl, aryl and heteroaryl, the latter 4 groups being optionally substituted, in the presence of ammonia $NH_3$ or an ammonia equivalent of the formula $NH_4^+X^-$, wherein X is an anionic ligand, wherein the amine of the formula Ia and/or Ib is produced in a yield of 50% or more.

2. The method according to claim 1, wherein $R^1$ and $R^2$ in the compounds of the formulae Ia, Ib and II are independently selected from $C_{1-10}$alkyl, $C_{2-10}$alkenyl, aryl and heteroaryl, all of which being optionally substituted; or $R^1$ and $R^2$ are linked to form an optionally substituted monocyclic or polycyclic ring system having 6 to 16 carbons including the carbonyl to which $R^1$ and $R^2$ are bonded and one or more of the carbons of the ring system is optionally replaced with a heteromoiety selected from O, S, N, $NR^{10}$ and $NR^{10}R^{11}$, in which $R^{10}$ and $R^{11}$ are independently selected from H, $C_{1-6}$alkyl and aryl.

3. The method according to claim 2, wherein $R^1$ and $R^2$ in the compounds of the formulae Ia, Ib and II are independently selected from methyl, ethyl, propyl, butyl, pentyl, ethene, styrene, phenyl, benzyl, thiophene and indole, all of which are optionally substituted.

4. The method according to claim 1, wherein $R^1$ and $R^2$ in the compounds of the formulae Ia, Ib and II are linked to form a ring system selected from cyclohexane, bicyclo[2.2.1]heptane, bicyclo[3.1.1]hept-2-ene and fluorene, all of which are optionally substituted, and one or more of the carbons of cyclohexane, bicyclo[2.2.1]heptane, bicyclo[3.1.1]hept-2-ene or fluorene is optionally replaced with a heteromoiety selected from O, S, N and $NR^{10}$; in which $R^{10}$ is H or benzyl.

5. The method according to claim 1, wherein the optional substituents on $R^1$ and $R^2$ in the compounds of the formulae Ia, Ib and II are independently selected from OH, halo, CN, $NO_2$, phenyl, benzyl, $OC_{1-6}$alkoxy, $C_{1-6}$alkyl, $C_{1-6}$alkenyl, $C_{1-6}$alkenyloxy, $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl, and $SC_{1-4}$alkyl.

6. The method according to claim 5, wherein the optional substituents on $R^1$ and $R^2$ in the compounds of the formulae Ia, Ib and II are independently selected from OH, F, Cl, Br, CN, $NO_2$, phenyl and $C_{1-4}$alkyl.

7. The method according to claim 1, wherein the optional substituents on $R^1$ and $R^2$ in the compounds of the formulae Ia, Ib and II further comprise at least one stereocenter.

8. The method according to claim 1, wherein $R^3$ to $R^7$ in the compounds of the formulae Ia, Ib and III are independently selected from H, $C_{1-10}$alkyl, $C_{3-12}$cycloalkyl, aryl and heteroaryl, the latter 4 groups being optionally substituted and one or more of the carbons in $C_{1-10}$alkyl and $C_{3-10}$cycloalkyl is optionally replaced with a heteromoiety selected from O, S, N, $NR^{10}$ and $NR^{10}R^{11}$ in which $R^{10}$ and $R^{11}$ are independently selected from H and $C_{1-6}$alkyl.

9. The method according to claim 8, wherein $R^3$ to $R^7$ in the compounds of the formulae Ia, Ib and III are independently selected from H and $C_{1-6}$alkyl.

10. The method according to claim 9, wherein $R^3$ to $R^7$ in the compounds of the formulae Ia, Ib and III are independently selected from H and methyl.

11. The method according to claim 1, wherein the optional substituents on $R^3$ and $R^7$ in the compounds of the formulae Ia, Ib and III are independently selected from OH, halo, CN, $NO_2$, phenyl, benzyl, $OC_{1-6}$alkoxy, $C_{1-6}$alkenyl, $C_{1-6}$alkenyloxy, $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl, and $SC_{1-4}$alkyl.

12. The method according to claim 1, wherein $R^8$ and $R^9$ in the compound of the formula III are independently selected from H, $C_{1-10}$alkyl, $C_{3-12}$cycloalkyl, aryl and heteroaryl, the latter 4 groups being optionally substituted; or $R^8$ and $R^9$ in the compound of the formula III are linked to form an optionally substituted monocyclic or polycyclic ring system having 5 to 12 atoms, including the B and O atoms to which $R^8$ and $R^9$ are bonded.

13. The method according to claim 12, wherein $R^8$ and $R^9$ in the compound of the formula III are independently selected from H or $C_{1-6}$alkyl; or $R^8$ and $R^9$ in the compound of the formula III are linked to form an optionally substituted monocyclic or bicyclic ring system having 5 to 12 atoms, including the B and O atoms to which $R^8$ and $R^9$ are bonded.

14. The method according to claim 1, wherein the optional substituents on $R^8$ and $R^9$ in the compound of the formula III are independently selected from OH, halo, CN, $NO_2$, phenyl, benzyl, $OC_{1-6}$alkoxy, $C_{1-6}$alkyl, $C_{1-6}$alkenyl, $C_{1-6}$alkenyloxy, $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl, and $SC_{1-4}$alkyl.

15. The method according to claim 14, wherein the optional substituent on $R^8$ and $R^9$ in the compound of the formula III is $C_{1-4}$alkyl.

16. The method according to claim 1, wherein X is selected from halo, $R^{12}COO$, $R^{12}SO_4$ and $BF_4$ in which $R^{12}$ is selected from $C_{1-10}$alkyl, $C_{3-20}$cycloalkyl, aryl and heteroaryl, all of which are optionally substituted; and wherein the optional substituents are independently selected from OH, halo, CN, $NO_2$, phenyl, benzyl, $OC_{1-6}$alkoxy, $C_{1-6}$alkyl, $C_{1-6}$alkenyl, $C_{1-6}$alkenyloxy, $NH_2$, $NH(C_{1-6}$alkyl), $N(C_{1-6}$alkyl)($C_{1-6}$alkyl), $C(O)C_{1-6}$alkyl, $C(O)OC_{1-6}$alkyl, $SO_2C_{1-6}$alkyl, $SO_2NH_2$, $SO_2NHC_{1-6}$alkyl, and $SC_{1-4}$alkyl.

17. The method according to claim 1, wherein the method is performed in the presence of ammonia.

18. The method according to claim 1, wherein the method is performed in an organic solvent.

19. The method according to claim 18, wherein the organic solvent is selected from methanol, ethanol, propanol, butanol, toluene, tetrahydrofuran, acetonitrile, benzene and methylene chloride.

20. The method according to claim 19, wherein the organic solvent is methanol.

21. The method according to claim 1, wherein the method is performed at a temperature of from −40° C. to +100° C.

22. The method according to claim 21, wherein the method is performed at room temperature.

* * * * *